(12) United States Patent
Black et al.

(10) Patent No.: US 10,094,796 B2
(45) Date of Patent: Oct. 9, 2018

(54) METHOD FOR NON-LINEAR HIGH SALINITY WATER CUT MEASUREMENTS

(71) Applicant: Saudi Arabian Oil Company, Dhahran (SA)

(72) Inventors: Michael John Black, Dhahran (SA); Mohamed Nabil Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/637,626

(22) Filed: Jun. 29, 2017

(65) Prior Publication Data

US 2018/0080893 A1    Mar. 22, 2018

Related U.S. Application Data

(62) Division of application No. 14/995,712, filed on Jan. 14, 2016.

(60) Provisional application No. 62/103,376, filed on Jan. 14, 2015.

(51) Int. Cl.
   *G01N 27/22* (2006.01)
   *G01N 33/28* (2006.01)
   *G01N 25/00* (2006.01)

(52) U.S. Cl.
   CPC .......... *G01N 27/221* (2013.01); *G01N 25/00* (2013.01); *G01N 33/2823* (2013.01); *G01N 33/2847* (2013.01)

(58) Field of Classification Search
   CPC ............. G01N 33/2847; G01N 27/221; G01N 33/2823; G01N 25/00

USPC ....... 324/693, 600, 694, 634–664, 689, 300, 324/315, 425, 431, 500, 750.03, 200, 224, 324/750.26, 750.28, 670; 702/25, 49–55, 702/100, 179

See application file for complete search history.

(56) References Cited

U.S. PATENT DOCUMENTS 6,076,049 A * 6/2000 Lievois ............. G01N 33/2823
                                                324/637
6,143,936 A   11/2000 Marion et al.
(Continued)

FOREIGN PATENT DOCUMENTS

GB   2376074 A      12/2002
WO   2007109772 A2  9/2007
(Continued)

OTHER PUBLICATIONS

Beer, Sebastian, et al. "In line monitoring of the preparation of water-in-oil (W/O/W) type multiple emulsions via dielectric spectroscopy" International Journal of Pharmaceutics 441 (2013); pp. 643-647.

(Continued)

*Primary Examiner* — Melissa Koval
*Assistant Examiner* — Trung Nguyen
(74) *Attorney, Agent, or Firm* — Bracewell LLP; Constance G. Rhebergen; Brian H. Tompkins (57) ABSTRACT

The present disclosure relates to a method for determining a water cut value of a composition comprising a hydrocarbon. In some embodiments, the disclosure relates to an apparatus for determining the water cut value of the composition that comprises one or more of a capacitance probe, a temperature probe, a salinity probe, and a computer.

2 Claims, 6 Drawing Sheets

(56) References Cited

U.S. PATENT DOCUMENTS

| | | | |
|---|---|---|---|
| 6,182,504 B1* | 2/2001 | Gaisford | G01F 1/74 324/634 |
| 6,831,470 B2 | 12/2004 | Xie et al. | |
| 6,886,632 B2 | 5/2005 | Raghuraman et al. | |
| 7,196,517 B2 | 3/2007 | Freedman | |
| 7,363,160 B2 | 4/2008 | Seleznev et al. | |
| 7,631,543 B2 | 12/2009 | Wee | |
| 7,908,930 B2 | 3/2011 | Xie et al. | |
| 7,958,939 B2* | 6/2011 | Talley | C09K 8/52 137/13 |
| 8,016,038 B2 | 9/2011 | Goodwin et al. | |
| 8,109,332 B2 | 2/2012 | Levy | |
| 8,329,965 B2 | 12/2012 | Matthews et al. | |
| 8,538,702 B2 | 9/2013 | Roy et al. | |
| 8,754,657 B2* | 6/2014 | Capone | G01N 33/2823 324/640 |
| 8,958,267 B2 | 2/2015 | Eick et al. | |
| 2007/0224692 A1 | 9/2007 | Agar et al. | |
| 2008/0015792 A1 | 1/2008 | Scott | |
| 2012/0041681 A1 | 2/2012 | Veneruso et al. | |
| 2012/0044784 A1 | 2/2012 | Pierle | |
| 2013/0002258 A1 | 1/2013 | Ligneul et al. | |
| 2013/0110411 A1 | 5/2013 | Black et al. | |
| 2013/0204534 A1 | 8/2013 | Anand et al. | |
| 2014/0210634 A1 | 7/2014 | Black et al. | |
| 2015/0100241 A1 | 4/2015 | Theune | |

FOREIGN PATENT DOCUMENTS

| | | |
|---|---|---|
| WO | 2007146357 A2 | 12/2007 |
| WO | 2015094318 A1 | 6/2015 |

OTHER PUBLICATIONS

Bruggeman, Von D.A.G; "Berechnung verschiedener physikalischer Konstanten von heterogenen Substanzen I. Dielektrizitaskonstanten and Leitfahigheiten der Mishkorper aus isotropen Substanzen" Annalen der Physik. 5. Folge. Band 24; 1935; pp. 636-679.

Garnett, J.C. Maxwell; "Colours in Metal Glasses and in Metallic Films" Trans. of the Royal Soc. (London) 203 (1904); pp. 385-420.

International Search Report and Written Opinion for Application No. PCT/US2016/013316 (SA5220/PCT); Report dated Apr. 14, 2016 (16 Pages).

Jackson, M.D., et al., "Laboratory Measurements and Numerical Modeling of Streaming Potential for Downhole Monitoring in Intelligent Wells" SPE 120460, SPE Middle East Oil and Gas Show and Conference, Mar. 15-18, 2009, pp. 625-636.

Meissner et al., "The Complex Dielectric Constant of Pure and Sea Water From Microwave Satellite Observations", Geoscience and Remote Sensing, 2004, pp. 1836-1849, vol. 42, No. 9, IEEE.

Sihvola, Ari; "Homogenization principles and effect of mixing on dielectric behavior" Photonics and Nanostructures—Fundamentals and Applications 11 (2013); pp. 364-373.

Sihvola, Ari; "Model Systems for Materials with High Dielectric Losses in Aquametry" Helsinki University of Technology, Electromagnetics Laboratory; Ch. 5; pp. 93-112.

Somaraju et al., "Frequency, Temperature and Salinity Variation of the Permittivity of Seawater", IEEE Transactions on Antennas and Propagation, vol. 54, No. 11, Nov. 2006, pp. 3441-3448.

Trukhan, E.M., "Dispersion of the Dielectric Constant of Heterogeneous Systems" Soviet Physics—Solid State; vol. 4, No. 12; Jun. 1963; pp. 2560-2570.

* cited by examiner

METHOD FOR NON-LINEAR HIGH SALINITY WATER CUT MEASUREMENTS

CROSS-REFERENCE TO RELATED PATENT APPLICATIONS

This application is a divisional of and claims priority to U.S. patent application Ser. No. 14/995,712, filed Jan. 14, 2016, which claims priority to and the benefit of U.S. Provisional Application No. 62/103,376, filed Jan. 14, 2015. For purposes of United States patent practice, this application incorporates the contents of each of the above Applications by reference in its entirety.

BACKGROUND

1. Field of the Disclosure

The field of disclosure relates to the production of hydrocarbon-based fluids. More specifically, the disclosure relates to a method for determining the water cut value for increasing the production of hydrocarbons from a reservoir, including enhanced oil recovery (EOR).

2. Description of the Related Art

The challenges associated with increasing the production of hydrocarbons such as crude oil in maturing production fields are well-established in the oil and gas industry. One solution for achieving EOR involves the use of water injection techniques, which can enhance the production of a reservoir by up to 50%. However, the use of water injection or "water cut" techniques can become economically unfeasible when a significant proportion of water is present relative to the corresponding volume of hydrocarbon, such as 80% water/20% hydrocarbon or greater. It would therefore be advantageous to develop accurate and informative methods for determining water and hydrocarbon ratios capable of both maximizing EOR and accounting for additional fluid, physicochemical conditions, and reservoir conditions, including but not limited to salinity and temperature.

It is known that when two materials, such as a hydrocarbon and water, with different permittivity values ($\in_1$ and $\in_2$) are mixed together that the resulting mixture permittivity ($\in_m$) is either $\in_m \ll$ both $\in_1$ and $\in_2$ or $\in_m \gg$ both $\in_1$ and $\in_2$. See S. Beer et al. "In-Line Monitoring of the Preparation of Water-in-Oil-in-Water (W/O/W) Type Multiple Emulsions via Dielectric Spectroscopy", *Int. J. Pharm.* 441 (2013) pp. 643-647 (hereinafter "Beer"). As described in Beer, evidence for the real presence of such a phenomenon is presented by a relative permittivity of 400 measured in conductive a W/O/W emulsion even though none of the individual components of the emulsion had a permittivity exceeding 80. In the case of a water-in-oil dual-phase fluid—a combination of two incompatible fluids that is often encountered downhole as part of a produced hydrocarbon-based composition—differences in mixture permittivity ($\in_m$) versus the real component of permittivity of either brines and crude oil alone is predicted to be a consequence of the presence of greater conductivities in the minority phase, which is brine or formation water. The greater conductivity of the minority phase manifests itself as the imaginary component to the detected permittivity of the mixture. See Sihvola, "Homogenization Principles and Effect of Mixing on Dielectric Behaviour", *Photon. Nanostruct: Fundam. Appl.* (2013).

Reduced frequency (≤1 MHz) permittivity measuring devices are based upon detecting the capacitance of a fluid. Two of the most applied models which are used to estimate $\in_m$ in such devices are variants of the Maxwell Garnet formula and the model proposed by D. A. G. Bruggeman. See C. Maxwell Garnet, "Colours in Metal Glasses and Metal Films," *Trans. of the Royal Soc.* (London) 203 (1904) pp. 385-420; D. A. G. Bruggeman, "Berechnung verschiedener physikalisches Konstanten von heterogenen Substanzen. I. Dielektrizitätskonstanten and Leitfähigkeiten der Mischkörper aus isotropen Substanzen", *Annalen der Physik* 24 (7-8) (1935) pp. 636-679 (hereinafter "Bruggeman").

Permittivity measuring devices are often calibrated with the assumption that the imaginary permittivity component of the fluid being tested does not provide a substantial contribution to detected mixture permittivity. This results in an assumption that the determined mixture permittivity behaves in a monotonic-type manner behavior as a function of increasing water cut ($\alpha$). The water cut value for a composition is the ratio of the amount of the aqueous portion of a composition to the amount of the non-aqueous portion, for example the hydrocarbon portion, where "0" represent a pure non-aqueous material and "1" represents a pure aqueous material. Water cut can be characterized as having a range of from 0 (no water) to 1 (all water).

The large imaginary component of permittivity, which originates from a greater-conductivity minority phase in the oil/water dual-phase fluid, can manifest itself as part of the mixture permittivity value. As outlined in Beer and in K. Kupfer (ed.), Electromagnetic Aquametry, Ch. 5, A. Sihvola "Model Systems for Materials with High Dielectric Losses in Aquametry", Springer, Heidelberg (2005) pp. 93-112, the inclusion of such a greater conductivity as a factor in mixture permittivity value ($\in_m$) results in what is characterized as non-monotonic behavior.

If one was to use the Bruggeman model and solve for the mixture permittivity value (Cm), the solution to the Bruggeman model that describes an even distribution of water droplets (an assumption for a minority phase of water evenly distributed in a majority phase of non-water) can be expressed as follows:

$$\in_m = \tfrac{1}{4}(2\in_1 - 3\alpha\in_1 - \in_2 + 3\alpha\in_2 + \sqrt{8\in_1\in_2 + (2\in_1 - 3\alpha\in_1 - \in_2 + 3\alpha\in_2)^2}) \quad \text{(Equation 1)}.$$

For a combination of hydrocarbons such as crude oil and water, solving for the permittivity value of pure crude oil is relatively easy. The real component of permittivity of a fluid is understood to be a measure of how much energy from an external electric field is stored in a material. Oil is generally assumed not to be conductive, so there are no energy losses from the fluid. Because there is no energy loss from the fluid acting as a capacitor, there no imaginary component of permittivity for a hydrocarbon fluid. The real component of permittivity value of crude oil (Re[$\in_{crude\_oil}$]), which is also the permittivity of crude oil ($\in_{crude\_oil}$), is equal to 3.

The determination of the complex permittivity of brine requires a more sophisticated calculation. The imaginary component of permittivity is associated with the conductivity of the material. Conductivity of a material is shown as the loss of energy from a material as energy is conveyed through the material instead of retained. Using a sodium chloride (NaCl) brine having a concentration of about 200,000 ppm NaCl (mass) at a temperature of 90° C., the conductivity of the brine ($\sigma_{brine}$) is about 50 S/m (Siemens/meter). A salinity value is the amount of dissolved salts in the composition in parts-per-million (ppm mass). The determined real permittivity component value of the brine (Re[$\in_{brine}$]) is about 50, which induces a frequency (f) of about 10,000 Hz (a reduced frequency) into the brine to produce a mixture permittivity ($\in_{brine}$) that allows for the empirical determination of the imaginary component of permittivity via back-calculation.

The calculation of the imaginary component of the permittivity of a brine ($\chi_{brine}$) with a known conductivity at a given frequency can also be performed using the following expression:

$$X_{brine} = \frac{\sigma_{brine}}{2\pi\varepsilon_0 f} = 8.99 \times 10^7, \quad \text{(Equation 2)}$$

where $\varepsilon_0 = 8.85 \times 10^{-12}$ F/m (Farad/meter), which is the known as the permittivity of free space. The calculated complex permittivity of the brine is:

$$\varepsilon_{brine} = Re[\varepsilon_{brine}] + i\chi_{brine} = 50 + 8.99 \times 10^7 i \quad \text{(Equation 3).}$$

Figure 1:
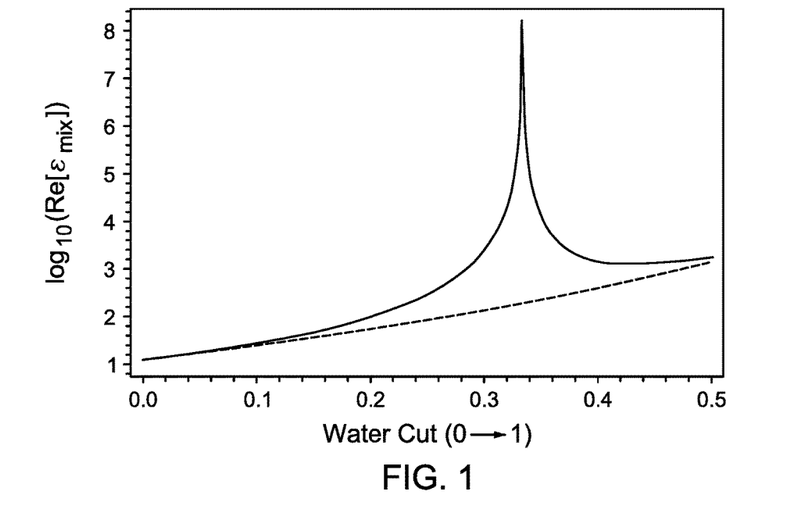
FIG. 1 shows the relationship between the determined real permittivity of a hydrocarbon-and-brine composition to its water cut value by introducing both oil and complex water permittivity functions into the Bruggeman model and by using a commercially-available water cut sensor that operates based on an approximation of the Bruggeman model.

FIG. 1 is a graph showing the relationship between the determined permittivity of a hydrocarbon-and-brine composition on a logarithmic scale ($\log_{10}(Re[\varepsilon_{mix}])$) to its water cut value by introducing both an oil and a complex water permittivity functions (including Equation 3) into the Bruggeman model (Equation 1) (solid line) and by using a commercially-available water cut sensor that uses an approximation of the Bruggeman model (dashed line). The testing frequency and salinity are fixed at the previously stated values (10,000 Hz and 50 S/m) while the water cut value is modified to produce the determined mixture permittivity. The water cut values range from 0 (100% hydrocarbon) to a value of 0.5 (50:50 hydrocarbon:brine).

As shown in FIG. 1, the presence of greater levels of conductance in the brine phase result in the presence of the non-linear peak for the determined real permittivity of the mixture that is in a range of from about 0.3 to about 0.4 for the water cut value ($\alpha$). The magnitude of the detected peak in mixture permittivity is about 100,000,000 ($\log_{10}=8$), which is a value that exceeds the maximum real permittivity component values for either brine or crude oil ($\varepsilon$=about 50 and 3, respectively). The large imaginary component of brine permittivity in this range suggests that the imaginary component cannot be ignored when determining the mixture permittivity of a dual-phase composition, especially one with a minor phase that is conductive, unlike what commercial permittivity sensors can determine.

Figure 2:
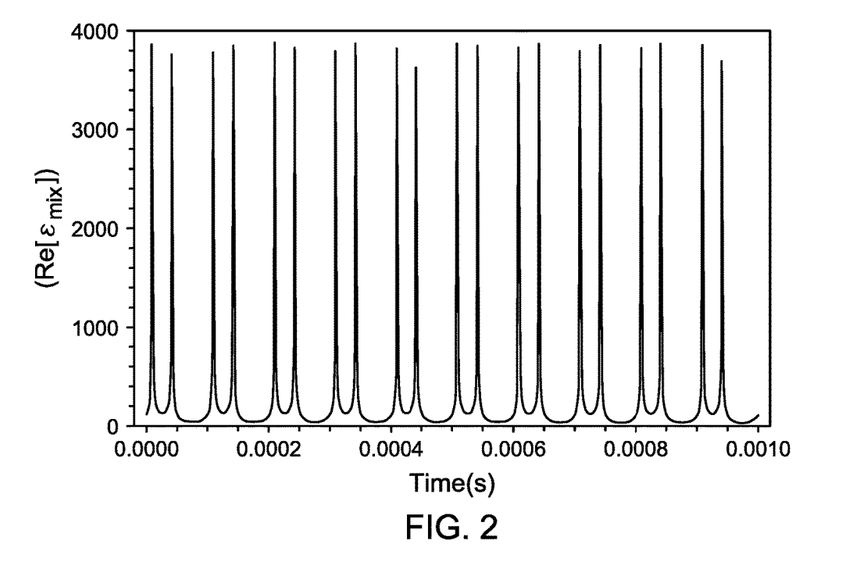
FIG. 2 shows the relationship between the determined real permittivity of the mixture when the value of the water cut is rapidly varied by 5% with time within the water cut value range of $\alpha$=0.3 to 0.4.

The other problem of using a method that relies on the assumption of a monotonic curve relationship for determining mixture permittivity is shown in FIG. 2. The existence of non-monotonic deviations in the determined mixture permittivity results in spurious "spikes", amplifications or "signal-doubling" of the determined permittivity mixture values. FIG. 2 is a graph showing the relationship between the determined permittivity of the mixture when the value of the water cut ($\alpha$) is rapidly varied by 5% with time within the water cut value range of $\alpha=0.3$ to 0.4, such as what would happen in a continuous production process of a crude oil-and-water composition. The signal-doubling occurs because the water cut value is varied across the peak of the determined mixture permittivity shown in FIG. 1. Such oscillations in mixture permittivity could lead a person of skill in the art to incorrectly conclude that dramatic water or brine slugging is occurring. The Bruggemann model, when used with complex crude oil and water permittivity functions, predicts such rapid increases in the mixture permittivity even with minor variations in the overall oil:brine ratio in the composition.

Depending on the model used to describe the permittivity function with relationship to salinity, frequency and water cut, or to the permittivity value of the mixture where the variables are fixed, different non-linear dependencies are encountered. Such non-linearity effects are only observed where the salinity of the brine is great enough to result in a conductivity that drives the imaginary component of permittivity to overwhelm both the real permittivity of the brine and the crude oil. The presence of such non-linear effects in a downhole hydrocarbon and conductive brine composition can be regarded as an example of a dielectric meta-material (where two or more dielectrics are arranged in a regular fashion). Just as excessive permittivity for a composition can be induced beyond each component's relative permittivity, losses due to excessive conductivity can be induced in a dielectric meta-material where neither component has any loss properties.

It is therefore desirable to be able to account for large non-linear effects of conductivity in the minor phase of a dual-phase fluid, such as a crude oil-brine composition. It is also useful to determine an estimate of the water cut value for the crude oil-brine composition based upon empirical or theoretical models that account for the imaginary components of mixture permittivity whether certain variables, including salinity value, are known or not.

SUMMARY

The present disclosure relates to methods method for determining a water cut value for a hydrocarbon composition for increasing the production of the hydrocarbon from a reservoir. The determined water cut value, in some embodiments, optimizes relevant properties such as the ratio of water to hydrocarbon in water cut applications for enhancing the production of hydrocarbons from a reservoir. The resulting properties in data, in some embodiments, can be introduced into, used to calibrate, or both oilfield equipment capable of regulating water and hydrocarbon ratios in water cut applications such as water cut meters. In some embodiments, the hydrocarbon composition is characterized by the water cut value and a salinity value. In further embodiments, the method includes inducing a non-zero frequency value into the hydrocarbon composition. In some embodiments, the method includes detecting a temperature value, a salinity value and a mixture permittivity value at the induced frequency value of the hydrocarbon composition. In certain embodiments, the method includes inducing a non-zero normalization frequency value into the hydrocarbon composition. In further embodiments, the method includes detecting a reference mixture permittivity value for the hydrocarbon composition at the induced normalization frequency value. In some embodiments, the method includes determining the water cut value of the hydrocarbon composition using a determined salinity value and a determined ratiometric mixed permittivity value of the hydrocarbon composition, and the induced frequency value.

In some embodiments, the present disclosure relates to a method for determining the water cut value and the salinity value of the hydrocarbon composition that includes obtaining the hydrocarbon composition. In certain embodiments, the hydrocarbon composition has the water cut value and the salinity value. In some embodiments, the method includes inducing a set of frequency values into the hydrocarbon composition in a range of from a first frequency value to a second frequency value. In further embodiments, the method includes detecting a set of mixture permittivity values at the set of induced frequency values. In still further embodiments, the method includes inducing a normalization frequency value into the hydrocarbon composition. In some embodiments, the method includes detecting a reference mixture permittivity value at the induced normalization frequency value. In certain embodiments, the method includes determining a set of ratiometric mixture permittivity values using the reference mixture permittivity value and the set of detected mixture permittivity values. In some embodiments, the method includes deriving a first set of ratiometric mixture permittivity values at the set of induced frequency values, a first set of salinity values and a first water cut value, where the first set of ratiometric mixture permittivity values is normalized at a first reference mixture permittivity value at the induced normalization frequency value. In further embodiments, the method includes deriving a second set of ratiometric mixture permittivity values at the set of induced frequency values, a second set of salinity values and a second water cut value, and the second set of ratiometric mixture permittivity values is normalized at a second reference mixture permittivity value at the induced normalization frequency value. In still further embodiments, the first water cut value and the second water cut value is not the same. In certain embodiments, the method includes determining the water cut value and the salinity value of the hydrocarbon composition by comparing the set of determined ratiometric mixture permittivity values to the first set of derived ratiometric mixture permittivity values and the second set of derived ratiometric mixture permittivity values at the set of induced frequency values.

In some embodiments, the disclosure relates to an apparatus for determining a water cut value of a hydrocarbon composition that includes a capacitance probe. In certain embodiments, the capacitance probe is in fluid contact with the hydrocarbon composition that is operable to induce a frequency value into the hydrocarbon composition, to detect a mixture permittivity value associated with the induced frequency value and to form an associated signal for the detected mixture permittivity value. In alternative embodiments, a resonant cavity, one or more dielectric coaxial probes or other means for detecting a mixture permittivity value can be incorporated in the apparatus. In certain embodiments, the apparatus includes a temperature probe that is in fluid contact with the hydrocarbon composition and is operable to detect the temperature value of the composition and to form an associated signal for the detected temperature value. In some embodiments, the apparatus includes a salinity probe that is optionally in fluid contact with the hydrocarbon composition, is operable to detect the salinity value of the composition and forms an associated signal for the detected salinity value.

In some embodiments, the apparatus includes a computer comprising a signal processing device having a non-transitory computer memory that is operable to receive associated signals for the detected mixture permittivity, the temperature and the salinity values of the hydrocarbon composition. In some embodiments, the computer comprises data stored on a readable medium and a programmed product stored in the non-transitory computer memory. In certain embodiments, the programmed product comprises instructions that are executable for converting the associated signals into detected mixture permittivity, temperature and salinity values, for associating the detected mixture permittivity value of the hydrocarbon composition with the induced frequency value, for converting the detected salinity value into a determined salinity value using data stored on the readable medium, for converting the detected mixture permittivity value into a determined ratiometric mixture permittivity value, for comparing the determined ratiometric mixture permittivity value at the determined salinity and induced frequency values with the data stored on the readable medium, and for determining the water cut value for the hydrocarbon composition. In some embodiments, one of the detected mixture permittivity values is the reference mixture permittivity values and is associated with the induced normalization frequency value.

The method and apparatus advantageously provide a more robust and reliable technique for determining the water cut value for a sample of hydrocarbon-based composition given the non-linearity mixture permittivity effects. When the conductivity of a co-produced brine or formation water is great in the hydrocarbon composition (relative to other formation-produced water or fresh water), the salinity of the composition is also great. A brine having a salinity of about 200,000 ppm (mass) is not uncommon. When salinity of the brine phase is great, substantial non-linearity effects are observed in the determined mixture permittivity. The non-linearity effects are reproducible. The method of determining the water cut value for a hydrocarbon composition uses ratiometric mixture permittivity values, either generated from empirical mixture permittivity values or theoretical mixture permittivity equations.

Equation 2, which is useful for determining the magnitude of the imaginary component of permittivity of brine, is a function of both salinity and the induced frequency used to determine the mixture permittivity of brine. If the frequency is varied, according to Equation 2, the expression of the magnitude of the imaginary component can be modulated. Reduced frequencies (non-zero frequencies in the 0-1 MHz range) therefore can both highlight and minimize the deviations observed in mixture permittivity through the imaginary component of mixture permittivity. The change in induced frequency value affects the real component of mixture permittivity, but the value of the imaginary component can be affected by orders of magnitude.

The approach towards the determination of water cut using ratiometric mixture permittivity should be less susceptible to measurement drift, and therefore reliability will be improved in determining the water cut measurement for hydrocarbon-based compositions downhole.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as they can admit to other equally effective embodiments.

DETAILED DESCRIPTION OF THE EMBODIMENTS

Although the following detailed description contains specific details for illustrative purposes, the skilled artisan will appreciate that many examples, variations and alterations to the following details are within the scope and spirit of the disclosure. Accordingly, the embodiments of the disclosure described in the disclosure and provided in the appended figures are set forth without any loss of generality, and without undue limitations, on the claims.

The term "couple" and its conjugated forms means to complete any type of required junction, including electrical, mechanical or fluid, to form a singular object from two or more previously non-joined objects. If a first device couples to a second device, the connection can occur either directly or through a common connector.

Spatial terms describe the relative position of an object or a group of objects relative to another object or group of objects. The spatial relationships apply along vertical and horizontal axes. Orientation and relational words, including "upstream" and "downstream", are for descriptive convenience and are not limiting unless otherwise indicated.

Where a range of values is provided, it is understood that the interval encompasses each intervening value between the first limit and the second limit as well as the first limit and the second limit. The disclosure encompasses and bounds smaller ranges of the interval subject to any specific exclusion provided.

"Detect" and its conjugated forms should be interpreted to mean the identification of the presence or existence of a characteristic or property. "Determine" and its conjugated forms should be interpreted to mean the ascertainment or establishment through analysis or calculation of a characteristic or property.

Where a method comprising two or more defined steps is described or referenced, the defined steps can be carried out in any order or simultaneously except where the context excludes that possibility.

When a reference including a patent, a patent application or non-patent literature is referenced in this disclosure, the reference is incorporated in its entirety to the extent that it does not contradict statements made in this disclosure.

The present disclosure advantageously produces water cut values and related information for increasing hydrocarbon production. For instance, the resulting water cut values and related information can be used for adjusting and calibrating water and hydrocarbon measurement tools, including but not limited to water cut meters, and to enhance directional drilling, production logging, structural steering, and related oilfield and downhole operations that ultimately result in EOR.

For a hydrocarbon composition, the determination of mixture permittivity ($\in_{mix}$) having complex components (both real and imaginary) is a function that depends on induced frequency (f), water cut ($\alpha$) and salinity of the brine ($\sigma_{brine}$). In determining mixture permittivity or associated variable values, any or all of these variables can be fixed, discrete values or sets of values. A "sweep" of induced frequencies includes frequency values from a first value to a second value, and all frequencies in the range. A set of values can also be a distinct and non-continuous set of values that can be between the first value and second value, inclusive of the first value and the second value, or both. A range of water cut values from 0.1 to 0.4 are often presented as discrete values at each tenth between 0.1 and 0.4, inclusive.

For a hydrocarbon composition, a detected mixture permittivity value is or a set of detected mixture permittivity values are associated with a discrete induced frequency value or a range of induced frequency values from a first induced frequency value to a second induced frequency value. All induced frequency values are non-zero because the frequency induced into the hydrocarbon composition prompts a detectable mixture permittivity response.

The hydrocarbon composition includes both an aqueous portion and a hydrocarbon portion. The aqueous portion comprises one or more of water, formation water, brine, synthetic or non-natural salt water and sea water having a detectable salinity value. The hydrocarbon portion of the hydrocarbon composition comprises one or more of the hydrocarbon-bearing fluids selected from crude oil, liquid condensate, crude oil atmospheric fractions, crude oil vacuum fractions, desalinated oil, synthetic and non-naturally occurring oil compositions, and combinations thereof.

For a hydrocarbon composition, a detected mixture permittivity value or set of detected mixture permittivity values are associated with a discrete water cut value or a range of water cut values from a first water cut value to a second water cut value. A water cut value of "0" represents a pure hydrocarbon material, including but not limited to crude oil, and a "1" represents a pure aqueous material (brine or formation water) for a hydrocarbon composition.

For a hydrocarbon composition, a detected mixture permittivity value or set of detected mixture permittivity values are associated with a discrete salinity value or a range of salinity values from a first salinity value to a second salinity value. Salts and formation minerals that are detectable as saline reside in the non-hydrocarbon phase of the hydrocarbon composition.

The mixture permittivity is a function of induced frequency, the salinity of the aqueous phase and the water cut of a hydrocarbon-containing composition. Models, equations and sets of empirically-derived data are useful for comparing to a measured or determined mixture permittivity value or set of values to determine one or more of the independent variables of permittivity (frequency, salinity, water cut) when the other variables are known. Depending on the comparison made, mathematical and statistical techniques, including looping-iterative calculations, variable substitution or solving, "curve fitting", "best fits" and "least squares", are known to one of ordinary skill in the art for solving or reducing errors to acceptable levels.

Figure 5:
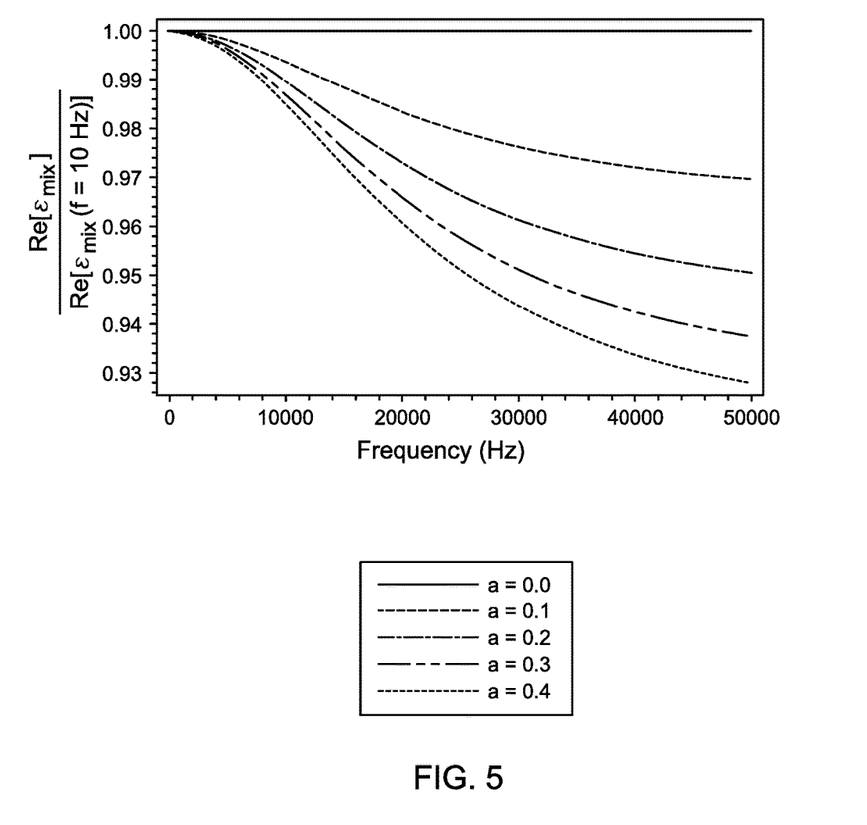
FIG. 5 shows a second ratiometric theoretical model of a complex mixture permittivity value equation at a fixed salinity value, at several distinct water cut values and over a range of induced frequencies.
Figure 6:
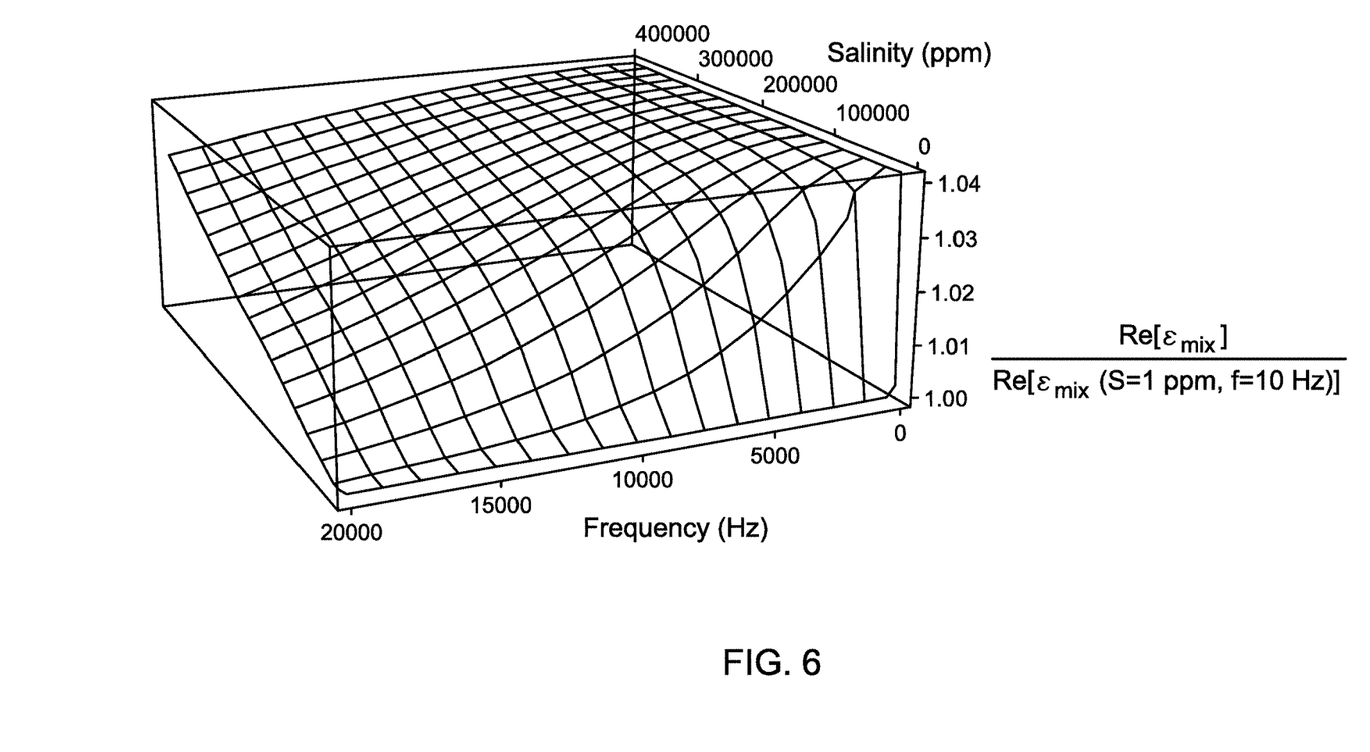
FIG. 6 shows a wireline surface of interpolated values using a ratiometric theoretical model of complex mixture permittivity value equation at a fixed water cut value ($\alpha=0.2$) for a range of salinity values and a range of induced frequency values.

A useful theoretical model of the complex mixture permittivity of a hydrocarbon composition accounts for the induced frequency, temperature-adjusted salinity and the water cut value of the composition. A useful complex theoretical model mixture permittivity value equation can be derived from the Bruggemann model (Equation 1 and FIGS. 1-4). In addition, a useful complex permittivity theoretical model mixture permittivity value equation can be derived from an interpretation of the of the model described by Trukhan ("Dispersion of the Dielectric Constant of Heterogeneous Systems", *Soviet Physics—Solid State* 4(12), 1963 pp. 2560-2570 (hereinafter "Trukhan")), as shown in FIGS. 5-6. The theoretical model equations are useful for presenting derived mixture permittivity values at various water cut, frequency and salinity values or ranges.

Figure 3:
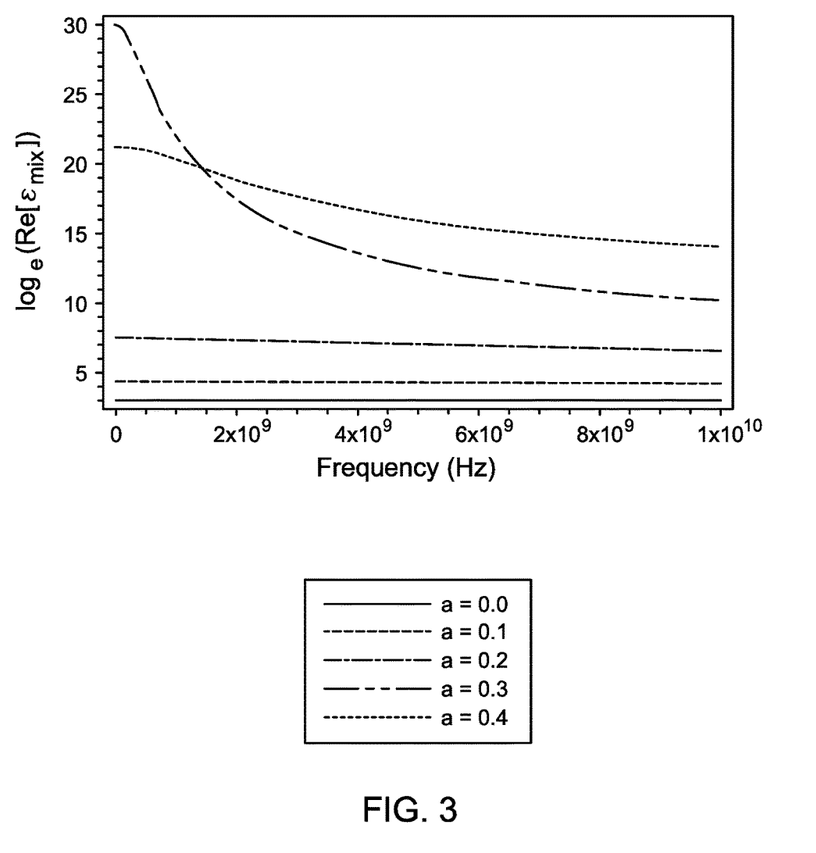
FIG. 3 shows a graphical representation of a complex permittivity theoretical model mixture permittivity value equation to represent the dependence of mixture permittivity as a function of frequency over a given frequency range for a represented hydrocarbon composition with fixed salinity and water cut values.

A complex permittivity theoretical model mixture permittivity value equation to represent the dependence of mixture permittivity ($\in_{mix}$) as a function of frequency (f) over a given frequency range (0 to $10 \times 10^9$ Hz) for a represented hydrocarbon composition with fixed salinity ($\sigma_{brine}$) and water cut ($\alpha$) values (FIG. 3). The individual plots in FIG. 3 represent complex permittivity theoretical model mixture permittivity value equations at a water cut value between $\alpha=0.0$ (all hydrocarbon fluid) and $\alpha=0.4$ (40:60 dual-phase water:hydrocarbon fluid) at distinct tenths inclusive using an interpretation of the Bruggeman model. Alternatively, the values in FIG. 3 can be derived using an empirically-determined mixture permittivity value equation or empirically-determined data of mixture permittivity, induced frequency, salinity and water cut values for a hydrocarbon composition.

An empirical model of the hydrocarbon composition mixture permittivity also accounts for induced frequency, temperature-adjusted salinity and water cut values. Like the theoretical model, an empirical model is also useful for determining unknown variable values, for instance water cut, using mathematical techniques when the other independent variable values are known. Useful empirically-determined mixture permittivity value equations can be experimentally or theoretically determined for model hydrocarbon compositions that are naturally occurring, synthetically formed, or both.

A set of derived mixture permittivity values from empirically-determined data is also useful for direct comparison to a determined mixture permittivity value. The empirically-determined data contains derived mixture permittivity and the associated induced frequency, temperature-adjusted salinity and water cut values for a hydrocarbon composition at that permittivity. Such information can be derived from the testing of model hydrocarbon compositions that are either naturally occurring or are synthetically formed, or both.

Mixture permittivity values are normalized at a reference permittivity value and a non-zero normalization frequency to form ratiometric mixture permittivity values. Normalizing the mixture permittivity value reduces uncertainty with respect to the calibration of and measurement by a permittivity measuring apparatus at an induced frequency value. The normalization frequency can be set within the range of frequency values for the set of mixture permittivity values being normalized.

In some embodiments, a mixture permittivity value equation used in accordance with the present disclosure is normalized with the reference mixture permittivity value at the non-zero normalization frequency to form a ratiometric mixture permittivity value equation. At the normalization frequency, the reference mixture permittivity value is determined using the equation, and the normalized function produces the ratiometric mixture permittivity value of 1 at the non-zero normalization frequency. For empirically-determined mixture permittivity data, the reference mixture permittivity value is present in a database and the normalization frequency is the associated frequency value.

In some embodiments, the ratiometric mixture permittivity values can be determined by varying both salinity values at a fixed frequency and water cut values or, in further embodiments, can be determined by varying both water cut values at a fixed frequency and salinity values.

Figure 4:
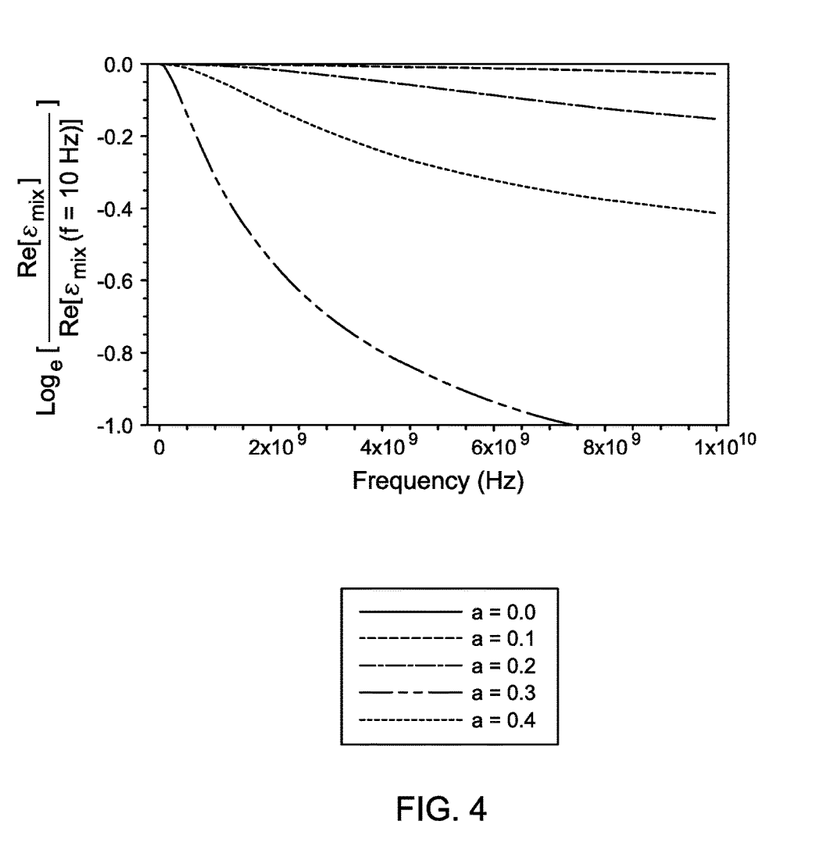
FIG. 4 shows the theoretical model of complex mixture permittivity value equations of FIG. 3 in ratiometric form on a logarithm scale.

FIG. 4 shows a theoretical model representation of the complex mixture permittivity value equations (at various water cut values) as depicted in FIG. 3. Each theoretical model equation is normalized using the reference mixture permittivity value determined using the equation at the non-zero normalization frequency of 10 Hz for each water cut value. As shown in FIG. 4, the ratiometric mixture permittivity value for each set of ratiometric mixture permittivity values is equal to 0 (the $\log_{10}$ of 1) at the non-zero normalization frequency. As the frequency increases and the water cut value increases to a value greater than 0, the corresponding ratiometric mixture permittivity values become less than 0.

FIG. 5 shows a second ratiometric theoretical model of complex mixture permittivity value equation at a fixed salinity value, several distinct water cut values and over a range of induced frequencies. The theoretical model of complex mixture permittivity used to generate FIG. 5 is based on Trukhan. Each ratiometric theoretical model of complex mixture permittivity value equation is normalized to 1 using the derived mixture permittivity value produced by each equation for distinct water cut values at a normalization frequency value of 10 Hz. FIGS. 4 and 5 demonstrate the effect of dielectric dispersion as the brine fraction increases and the frequency becomes greater.

Developing sets of ratiometric mixture permittivity values, either through equations or empirically-derived data at associated induced frequencies, water cut values and salinity values is useful for developing a three-dimensional wireline surface representation of interpolated mixture permittivity values using a ratiometric theoretical model of complex mixture permittivity value equation at a fixed water cut value ($\alpha=0.2$) for a range of salinity values and a range of induced frequency values as shown in FIG. 6. The ratiometric theoretical model of complex mixture permittivity value equation is based on Trukhan and normalized using the reference mixture permittivity value determined at the normalization frequency of 10 Hz and a normalization salinity of 1 ppm. A three-dimensional wireline structure representing the relationship between a ratiometric mixture permittivity value, a frequency value and water cut value at a fixed salinity value is useful when the brine salinity is known, for example in a geographic area or a hydrocarbon reservoir.

Figure 7:
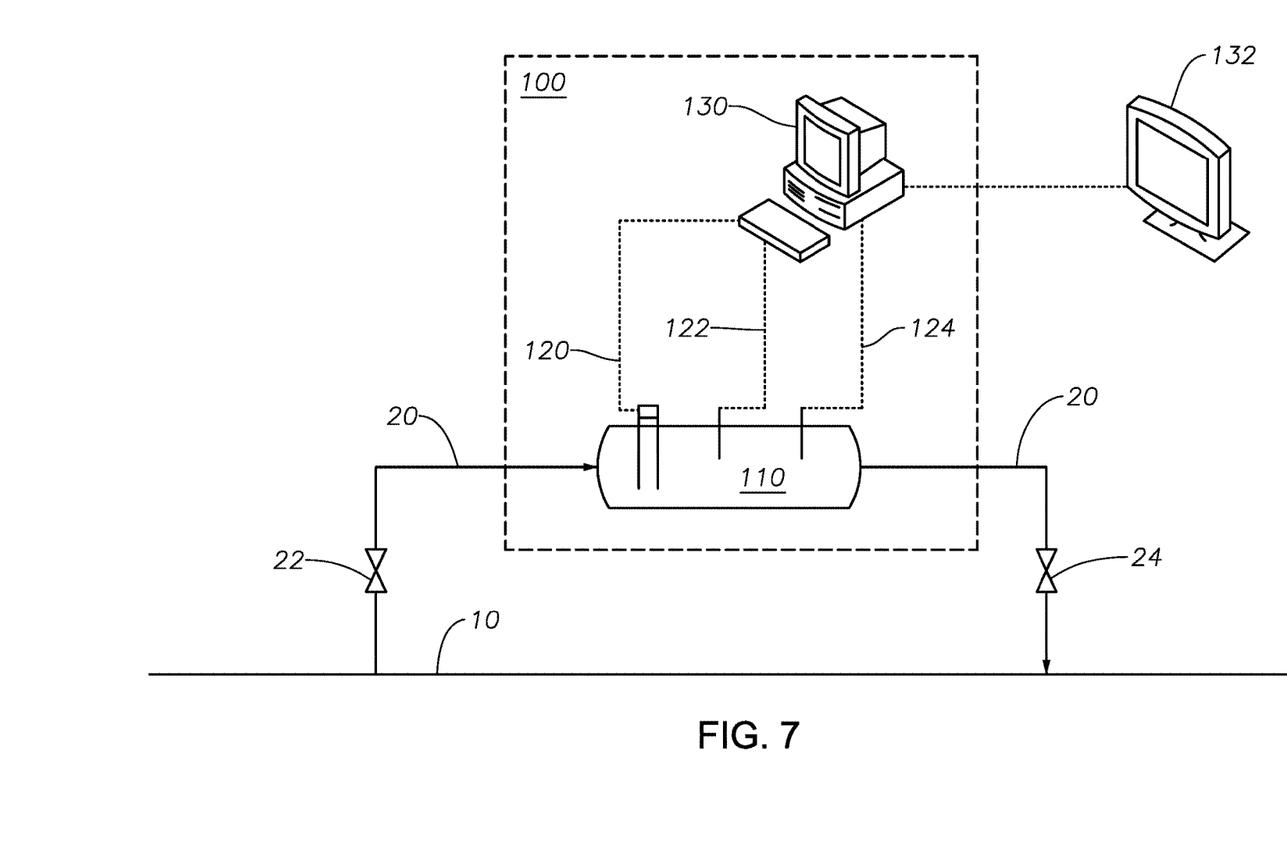
FIG. 7 shows an apparatus that is useful for determining the water cut value of the hydrocarbon composition.

FIG. 7 shows an apparatus for determining the water cut value of a hydrocarbon composition. A process line 10 operably connected to a testing apparatus 100 transfers the hydrocarbon composition from a first location to a second location (not shown). A portion of the hydrocarbon composition is delivered intermittently or in a continuous flow of fluid to a testing apparatus 100 through process lines 22 and 20. The hydrocarbon composition is delivered to testing apparatus 100 and introduced into testing vessel 110. The testing vessel 110 is optionally a single vessel coupled to sample bypass line 20, a wider portion of the pipe or tubing or a continuous portion of the pipe or tubing making up the process line 20 and, in some embodiments, comprises coupled sensors that traverse the wall of the pipe or tubing. The hydrocarbon composition sample passes from testing vessel 110 into the process line 10 via the downstream portion 24 of the sample bypass line 20.

The sample hydrocarbon composition flowing through testing vessel 110 can be subjected to several non-destructive tests for determining various properties of the hydrocarbon composition sample. For instance, in some embodiments a capacitance probe 120 operably contacts a hydrocarbon composition and induces a frequency value into the composition for determining the mixture permittivity value associated with the induced frequency value and producing an associated signal for the detected mixture permittivity value or range of values. In further embodiments, a temperature probe 122 operably contacts a hydrocarbon composition for detecting the temperature of the composition and producing an associated signal for the detected temperature value. In still further embodiments, a salinity probe 124 operably contacts a hydrocarbon composition for detecting the salinity of the composition and producing an associated signal for the detected salinity value. In some embodiments, a further probe capable of performing as a dedicated frequency probe can act as a standard or control to ensure the proper function of the apparatus while in service.

A capacitance probe 120, a temperature probe 122 and a salinity probe 124 in accordance with the present disclosure are operably engaged with a computer 130. The testing apparatus 100 ensures that the capacitance probe 120, the temperature probe 122 and the salinity probe 124 transmit associated signals, continuously or intermittently, for the hydrocarbon composition properties and conditions of interest to the computer 130. The computer 130 optionally includes a signal processing device and a non-transitory computer memory.

In some embodiments, the computer 130 is capable of determining the ratiometric mixture permittivity value using one or more of the theoretical model of complex ratiometric mixture permittivity value equation, the empirically-determined ratiometric mixture permittivity value equation, the empirically-determined data of ratiometric mixture permittivity, induced frequency, salinity values including detected salinity values and determined salinity values, associated temperature values and water cut values for the hydrocarbon composition to determine the water cut value for the hydrocarbon composition. The resulting data and water cut values may be utilized, for instance, in oilfield control operations and equipment, including but not limited to the calibration of a water cut meter.

In some embodiments, the computer 130 converts the detected salinity value into a determined salinity value using the detected temperature value. The detected salinity value is known to be temperature sensitive, and in certain embodiments the computer 130 can adjust the determined salinity value to account for temperature.

The computer 130 is further capable of converting the associated signals from the capacitance probe 120, the temperature probe 122 and the salinity probe 124 into mixture permittivity, temperature and salinity values for the hydrocarbon composition, for one or more of (1) associating the detected mixture permittivity value of the hydrocarbon composition with the induced frequency value; (2) converting the detected salinity value into a determined salinity value using data stored on a readable medium; (3) converting the detected mixture permittivity value into a determined ratiometric mixture permittivity value; (4) comparing the determined ratiometric mixture permittivity value at the determined salinity and induced frequency values with the data stored on the readable medium; and (5) determining the water cut value for the hydrocarbon composition.

The apparatus of the present disclosure can induce a frequency into the sample hydrocarbon composition using capacitance probe 120, in either a static or sweeping manner, up to about 1 MHz. The apparatus can further comprise more than one capacitance probe with different geometric design (such as different surface area, spacing within the apparatus, or both) for parallel detected mixture permittivity measurements at different induced frequencies or different induced frequency ranges simultaneously. The array of different capacitance probes, each testing at a specific frequency value, avoids time-based frequency sweeps and provides instantaneous mixture permittivity data.

In an embodiment of the method, the induced normalization frequency is a non-zero frequency value, or about 10 Hz, or about 1000 Hz. In an embodiment of the method, the frequency is induced sweepingly into the hydrocarbon composition having a range of frequency values up to about 20 kHz, or up to about 1 MHz. In an embodiment of the method, the normalization salinity is a non-zero value, or about 1 ppm.

Although the present disclosure has been described in detail, it should be understood that various changes, substitutions, and alterations can be made hereupon without departing from the principle and scope of the disclosure. Accordingly, the scope of the present disclosure should be determined by the following claims and their appropriate legal equivalents.

The singular forms "a", "an" and "the" include plural references, unless the context clearly dictates otherwise.

"Optional" or "optionally" means that the subsequently described component can or cannot be present or the event or circumstances can or cannot occur. The description includes instances where the component is present and instances where it is not present, and instances where the event or circumstance occurs and instances where it does not occur.

Ranges can be expressed in the disclosure as from about one particular value, to about another particular value, or both. When such a range is expressed, it is to be understood that another embodiment is from the one particular value, to the other particular value, or both, along with all combinations within said range.

Throughout this application, where patents or publications are referenced, the disclosures of these references in their entireties are intended to be incorporated by reference into this application, in order to more fully describe the state of the art to which the disclosure pertains, except when these references contradict the statements made in the disclosure.

What is claimed is:

1. A method for determining a water cut value and a salinity value for a hydrocarbon composition, the method comprising the steps of:

obtaining the hydrocarbon composition, where the hydrocarbon composition has the water cut value and the salinity value;

inducing, by a capacitance probe, a set of frequency values into the hydrocarbon composition in a range of from a first frequency value to a second frequency value, the capacitance probe in fluid contact with the hydrocarbon composition;

detecting, by the capacitance probe, a set of mixture permittivity values of the hydrocarbon composition at the set of induced frequency values, the capacitance probe operable to form an associated signal for the set of mixture permittivity values;

inducing, by the capacitance probe, a normalization frequency value into the hydrocarbon composition;

detecting, by the capacitance probe, a reference mixture permittivity value at the induced normalization frequency value;

determining, at a computer coupled to the capacitance probe, a set of ratiometric mixture permittivity values using the reference mixture permittivity value and the set of detected mixture permittivity values, the computer comprising a signal processing device operable to receive the associated signal;

deriving, at the computer, a first set of ratiometric mixture permittivity values at the set of induced frequency values, a first set of salinity values and a first water cut value, where the first set of ratiometric mixture permittivity values is normalized at a first reference mixture permittivity value determined at the induced normalization frequency value;

deriving, at the computer, a second set of ratiometric mixture permittivity values at the set of induced frequency values, a second set of salinity values and a second water cut value, where the second set of ratiometric mixture permittivity values is normalized at a second reference mixture permittivity value determined at the induced normalization frequency value and where the first water cut value and the second water cut value are not the same; and determining, at a signal processing device, the water cut value and the salinity value of the hydrocarbon composition by comparing the set of determined ratiometric mixture permittivity values to the first set of derived ratiometric mixture permittivity values and the second set of derived ratiometric mixture permittivity values at the set of induced frequency values;

calibrating a water cut meter based on the determined water cut value; and using the water cut meter in an enhanced oil recovery (EOR) operation.

2. The method of claim 1 where the induced normalization frequency value is not within the set of induced frequency values.

* * * * *